United States Patent
Markert et al.

(10) Patent No.: US 6,864,225 B2
(45) Date of Patent: Mar. 8, 2005

(54) CYCLIC KETALS, FRAGRANCE COMPOSITIONS CONTAINING THE SAME AND METHODS OF USING THE SAME

(75) Inventors: Thomas Markert, Monheim (DE); Theo Ten Pierik, Le Venio (NL); Werner Faber, Willich (DE)

(73) Assignee: Kao Corporation, Tokyo (JP)

( * ) Notice: Subject to any disclaimer, the term of this patent is extended or adjusted under 35 U.S.C. 154(b) by 163 days.

(21) Appl. No.: 10/275,532

(22) PCT Filed: Apr. 28, 2001

(86) PCT No.: PCT/EP01/04821

§ 371 (c)(1),
(2), (4) Date: Nov. 5, 2002

(87) PCT Pub. No.: WO01/85713

PCT Pub. Date: Nov. 15, 2001

(65) Prior Publication Data

US 2003/0130164 A1 Jul. 10, 2003

(51) Int. Cl.⁷ .................................................. A61K 7/46
(52) U.S. Cl. .......................... 512/25; 512/12; 512/13; 512/20; 549/200; 549/356; 549/357; 549/358; 549/429; 549/430; 549/456
(58) Field of Search .............................. 512/20, 25, 12, 512/13; 549/200, 356, 357, 358, 429, 430, 456

(56) References Cited

U.S. PATENT DOCUMENTS

| | | | |
|---|---|---|---|
| 4,198,323 A | * | 4/1980 | Conrad et al. ................. 512/12 |
| 5,175,143 A | * | 12/1992 | Newman et al. ............... 512/12 |
| 6,114,301 A | * | 9/2000 | Kappey et al. ................ 512/12 |
| 6,297,390 B1 | | 10/2001 | Markert et al. |
| 6,376,457 B1 | | 4/2002 | Markert et al. |

FOREIGN PATENT DOCUMENTS

| | | |
|---|---|---|
| DE | 197 14 041 A1 | 10/1998 |
| DE | 197 29 840 A1 | 1/1999 |
| EP | 0 276 998 B1 | 8/1988 |

OTHER PUBLICATIONS

Database Specinfo Online! U.S. Doc; CAS Registry No. 74752–98–0, 1995 XP002173658.

* cited by examiner

*Primary Examiner*—Monique T. Cole
(74) *Attorney, Agent, or Firm*—Oblon, Spivak, McClelland, Maier & Neustadt, P.C.

(57) ABSTRACT

Compounds of the general formula (I) are described:

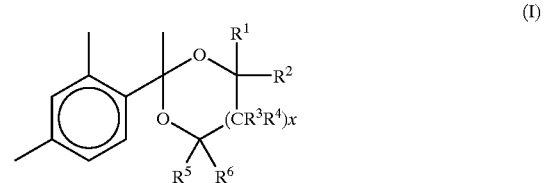

wherein each of $R^1$, $R^2$, $R^3$, $R^4$, $R^5$ and $R^6$ independently represents a substituent selected from the group consisting of hydrogen, methyl, ethyl, n-propyl, and isopropyl; an wherein x represents either 0 or 1. The compounds are useful as fragrances and as added components in fragrance blends. Methods of improving the harmony, emanation, naturalness an staying power of other fragrance ingredients by the addition of such compounds are also described.

18 Claims, No Drawings

CYCLIC KETALS, FRAGRANCE COMPOSITIONS CONTAINING THE SAME AND METHODS OF USING THE SAME

BACKGROUND OF THE INVENTION

Judging by demand, many natural perfumes are available in totally inadequate quantities. For example, 5,000 kg of rose blossoms are required to produce 1 kg of rose oil. The consequences are extremely limited annual world production and a high price. Accordingly, it is clear that there is a constant need in the perfume industry for new perfumes with interesting fragrance notes. On the one hand, the range of naturally available perfumes can be extended in this way; on the other hand, it is thus possible to make the necessary adaptations to changing fashion trends. In addition, it is possible in this way to meet the steadily increasing demand for odor enhancers for products of everyday use, such as cosmetics and cleaners.

In addition, there is generally a constant need for synthetic perfumes which can be favorably produced in a consistent quality and which have original olfactory properties, i.e. in particular pleasant, near-natural and qualitatively new odor profiles of adequate intensity, and which are capable of advantageously influencing the fragrance of cosmetic and consumer products. In other words, there is a constant need for compounds which have characteristic new odor profiles coupled with high staying power, intensity of odor and emanative power.

DE-A-197 14 041 describes special phenone ketals with flowery, anthranilate, ylang and tuberose notes which may be used as perfumes. Structurally, these special phenone ketals are open-chain ketals in contrast to the compounds according to the present invention.

BRIEF SUMMARY OF THE INVENTION

The present invention relates, in general, to new cyclic ketals with a special structure and to their use as perfumes.

It has been found that the compounds corresponding to general formula (I) excellently satisfy the above-mentioned requirements in every respect and may advantageously be used as perfumes with differently nuanced perfume notes characterized by high staying power.

In a first embodiment, the present invention relates to cyclic ketals corresponding to general formula (I):

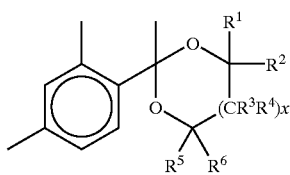

(I)

in which the substituents $R^1$ to $R^6$ independently of one another represent hydrogen, methyl, ethyl, n-propyl or i-propyl and x is the number 0 or 1. It is expressly pointed out that, when the index x is the number 0, the two carbon atoms which the substituents $R^1$ and $R^2$ and the substituents $R^5$ and $R^6$ carry are directly attached to one another.

In a preferred embodiment of the invention, the substituents $R^1$ to $R^6$ in general formula (I) independently of one another represent hydrogen or methyl.

In another embodiment, the present invention relates to the use of cyclic ketals corresponding to general formula (I) above as perfumes. In preferred compounds of formula (I), the substituents $R^1$ to $R^6$ independently of one another represent hydrogen or methyl.

DETAILED DESCRIPTION OF THE INVENTION

The compounds (I) according to the invention are distinguished by a perfume characteristic in which orange blossom notes and fuity and woody aspects dominate. They show excellent stability in cosmetic and consumer perfumery formulations.

The compounds (I) may be prepared by known synthesis processes of organic chemistry.

In perfume compositions, the compounds (I) strengthen harmony, emanation, naturalness and also staying power, the quantities used being adapted to the particular perfume note required taking the other ingredients of the composition into account.

The fact that the compounds (I) have the above-mentioned perfume notes was not foreseeable and, hence, is further confirmation of the general experience that the olfactory properties of known perfumes do not allow any definitive conclusions to be drawn as to the properties of structurally related compounds because neither the mechanism of odor perception nor the influence of chemical structure on odor perception has been sufficiently researched, so that it is not normally possible to predict whether modifications to the structure of known perfumes will in fact lead to changes in their olfactory properties or whether these changes will be positive or negative.

By virtue of their odor profile, the compounds corresponding to formula (I) are also particularly suitable for modifying and enhancing known compositions. Particular emphasis is placed on their extreme intensity of odor which contributes quite generally towards refining the composition.

The compounds corresponding to formula (I) may be combined with many known perfume ingredients, for example other perfumes of natural, synthetic or partly synthetic origin, essential oils and plant extracts. The range of natural fragrances can thus include both high-volatility and also medium-volatility and low-volatility components while the range of synthetic perfumes may include representatives of virtually every class of compounds.

Examples of suitable substances with which the compounds (I) may be combined are, in particular, (a) natural products, such as tree moss absolue, basil oil, citrus oils, such as bergamot oil, mandarin oil, etc., mastix absolue, myrtle oil, palmarosa oil, patchouli oil, petitgrain oil, wormwood oil, myrrh oil, olibanum oil (b) alcohols, such as farnesol, geraniol, linalool, nerol, phenylethyl alcohol, rhodinol, cinnamic alcohol, sandalore [3-methyl-5-(2,2,3-trimethylcyclopent-3-en-1-yl)-pentan-2-ol], sandela [3-isocamphyl-(5)-cyclohexanol]

(c) aldehydes, such as citral, Helional®, α-hexyl cinnamaldehyde, hydroxycitronellal, Lilial® [p-tert.butyl-α-methyldihydrocinnamalde-hyde], methylnonyl acetaldehyde (d) ketones, such as allylionone, α-ionone, β-ionone, isoraldein, methyl ionone, muscone (e) esters, such as allylphenoxyacetate, benzyl salicylate, cinnamyl propionate, citronellyl acetate, decyl acetate, dimethylbenzyl carbinyl acetate, ethyl acetoacetate, hexenyl isobutyrate, linalyl acetate, methyl dihydrojasmonate, vetiveryl acetate, cyclohexyl salicylate, isobornyl acetate, (f) lactones, such as gamma-undecalactone, 1-oxaspiro[4.4]-nonan-2-one and various other components often used in perfumery, such as musk and sandalwood perfumes, indole, p-methan-8-thiol-3-one, methyl eugenol and Ambroxan.

It is also remarkable how the compounds corresponding to formula (I) round off and harmonize the odor notes of a broad range of known compositions without unpleasantly dominating them in any way. 2,4-Dimethyl-2-(2,4-dimethylphenyl)-1,3-dioxolane is particularly emphasized in this regard.

The compounds (I) according to the invention or mixtures thereof may be used in perfume compositions in quantities of about 1 to 70% by weight, based on the mixture as a whole. Mixtures of compounds (I) according to the invention and compositions of this type may be used both for perfuming cosmetic preparations, such as lotions, creams, shampoos, soaps, emollients, powders, aerosols, toothpastes, mouthwashes, deodorants, and also in alcohol-based perfumery (for example colognes, toilet waters, extracts). The compounds according to the invention or mixtures thereof may also be used for perfuming commercial products, such as detergents, fabric softeners and textile treatment preparations. For perfuming these various products, the compositions are added in an olfactorily effective quantity, more particularly in a concentration of 0.05 to 2% by weight, based on the product as a whole. However, these values are not intended to represent limits because the experienced perfumer can also obtain effects with even lower concentrations or can build up new complexes with even higher doses.

EXAMPLES

Example 1
2-Methyl-2-(2,4-dimethylphenyl)-1,3-dioxolane
Materials:
a) 74.1 g (0.5 mol) 2,4-dimethyl acetophenone (Fluka)
b) 31.8 g (0.51 mol) ethylene glycol (1,2-ethanediol)
c) 0.5 g p-toluenesulfonic acid monohydrate (Fluka)
d) 150 ml toluene The four components a) to d) were successively introduced into a 0.5-litre four-necked flask equipped with a stirrer, thermometer and water separator, heated with stirring to reflux temperature (122° C.) and stirred at that temperature for 27 hours. By that time 10 ml water had separated off. The reaction mixture was cooled, washed until neutral, dried over $MgSO_4$, concentrated in a rotary evaporator and the residue was distilled in a 30 cm packed column. 79 g of distillate were obtained; the main fraction had a gas chromatographic (GC) purity of 100% for a boiling point of 79–82° C./0.14 mbar. The $^1$H-NMR spectrum showed 3 singlets (per 1 $CH_3$) group for chemical shifts of 1.7, 2.3 and 2.5 ppm, 2 $CH_2$ groups as symmetrical multiplets at 3.7 and 4.0 ppm and aromatic protons at 6.9 (2H) and 7.4 (d, 1H) ppm. The IR spectrum showed strong ether bands at 1038 and 1193 and benzene fingers at 822 and 866 $cm^{-1}$.
Perfume Characteristic:
Initial perfume flowery, tar, leather, oak moss, naphthalene; after-perfume herby, anthranilate note.

Example 2
2,4-Dimethyl-2-(2,4-dimethylphenyl)-1,3-dioxolane
Materials:
a) 74.0 g (0.5 mol) 2,4-dimethyl acetophenone (ABCR)
b) 41.9 g (0.55 mol) 1,2-propanediol (Merck)
e) 0.5 g p-toluenesulfonic acid monohydrate (Fluka)
f) 150 ml toluene The four components a), b), e) and f) were successively introduced into a 0.5-litre four-necked flask equipped with a stirrer, thermometer and water separator, heated with stirring to reflux temperature (130° C.) and stirred at that temperature for 6 hours. By that time 10 ml water had separated off. The reaction mixture was cooled, washed until neutral, dried over $MgSO_4$, concentrated in a rotary evaporator and 121 g of residue were distilled in a 30 cm packed column. 79 g of distillate were obtained; the main fraction had a gas chromatographic (GC) purity of 99% (two peak areas a' 63% +36%) for a boiling point of 84–85° C./0.14 mbar. The $^1$H-NMR spectrum showed 3 singlets (2 $CH_3$ groups) for chemical shifts of 2.3 and 2.5 ppm, 3 doublets at 1.2 and 1.4 (1 $CH_3$ group) and 1.7 (1 $CH_3$ group) ppm and, between 3.3 and 4.4 ppm, several triplets and multiplets (3 Hs) and aromatic protons at 6.9 (2 H) and 7.4 (d, 1 H) ppm. The reaction product was a mixture of two isomers which accumulated in a ratio of 2:1. The IR spectrum showed broad ether bands at 936, 952, 1038, 1063, 1084, 1152, 1193 and 1239 $cm^{-1}$.
Perfume Characteristic:
Initial perfume very fruity, cassis, nitro musk note; after-perfume anthranilate, salicylate, smoke note.

Example 3
2-Methyl-2-(2,4-dimethylphenyl)-1,3-dioxane
Materials:
a) 74.0 g (0.5 mol) 2,4-dimethyl acetophenone (ABCR)
b) 41.8 g (0.55 mol) 1,3-propanediol (Merck)
g) 0.5 g p-toluenesulfonic acid monohydrate (Fluka)
h) 150 ml toluene The four components a), b), g) and h) were successively introduced into a 0.5-litre four-necked flask equipped with a stirrer, thermometer and water separator, heated with stirring to reflux temperature (125° C.) and stirred at that temperature for 24 hours. By that time 12.5 ml water had separated off. The reaction mixture was cooled, washed until neutral, dried over $MgSO_4$, concentrated in a rotary evaporator and 90 g of residue were distilled in a 30 cm packed column. 57 g of distillate were obtained; the main fraction had a gas chromatographic (GC) purity of 97% for a boiling point of 90–94° C./0.12 mbar. The $^1$H-NMR spectrum showed 3 singlets (3 $CH_3$ groups) for chemical shifts of 1.5, 2.3 and 2.4 ppm and at, 3.8, multiplets (3 $CH_2$ groups) and aromatic protons at 7.0 (2 H) and 7.35 (d, 1H) ppm. The IR spectrum showed 8 sharp bands between 900 and 1200 $cm^{-1}$.
Perfume Characteristic:
Initial perfume flowery, metallic, rhubarb note; after-perfume weak, of anthranilate.

Example 4
2,5,5-Trimethyl-2-(2,4-dimethylphenyl)-1,3-dioxane
Materials:
a) 74.0 g (0.5 mol) 2,4-dimethyl acetophenone (ABCR)
b) 57.2 g (0.55 mol) neopentyl glycol (Cognis)
i) 0.5 g p-toluenesulfonic acid monohydrate (Fluka)
j) 150 ml toluene The four components a), b), i) and j) were successively introduced into a 0.5-litre four-necked flask equipped with a stirrer, thermometer and water separator, heated with stirring to reflux temperature (130° C.) and stirred at that temperature for 24 hours. By that time 5 ml water had separated off. The reaction mixture was cooled, washed until neutral, dried over $MgSO_4$, concentrated in a rotary evaporator and 126 g of residue were distilled in a 30 cm packed column. 77 g of distillate were obtained; the main fraction had a gas chromatographic (GC) purity of 100% for a boiling point of 104–105° C./0.15 mbar. The $^1$H-NMR spectrum showed 5 singlets (5 CH₃ groups) for chemical shifts of 0.6, 1.3, 1.5, 2.3 and 2.4 and, at 3.4, 1 quadruplet (2 CH₂ groups) and aromatic protons at 7.0 (2H) and 7.35 (d, 1H) ppm. The IR spectrum showed sharp ether bands between at 1082 and 1179 cm⁻¹.

Perfume Characteristic:
Initial perfume fruity, cassis, eucalyptus, ionone note; after-perfume weak, of eucalyptus.

Example 5
2,5-Dimethyl-5-propyl-2-(2,4-dimethylphenyl)-1,3-dioxane

Materials:
a) 74.0 g (0.5 mol) 2,4-dimethyl acetophenone (ABCR)
b) 72.6 g (0.55 mol) 2-methyl-2-propyl-1,3-propanediol (Cognis)
e) 0.5 g p-toluenesulfonic acid monohydrate (Fluka)
f) 150 ml toluene The four components a), b), k) and l) were successively introduced into a 0.5-litre four-necked flask equipped with a stirrer, thermometer and water separator, heated with stirring to reflux temperature (130° C.) and stirred at that temperature for 5 hours. By that time 7.5 ml water had separated off. The reaction mixture was cooled, washed until neutral, dried over MgSO₄, concentrated in a rotary evaporator and 141.6 g of residue were concentrated in a 30 cm packed column. 77 g of distillate were obtained; the main fraction had a gas chromatographic purity of 96.9% (two peak areas a' 52.6% +44.3%) for a boiling point of 100–105° C./0.07 mbar. The ¹H-NMR spectrum showed 5 singlets (4 CH₃ groups) for chemical shifts of 0.5, 1.3, 1.5, 2.3 and 2.4 ppm, 2 triplets at 0.8 and 1.0 ppm (1 CH₃ group) and multiplets at 0.9, 1.1, 1.3 and 1.7 ppm (2 CH₂ groups) and, at 3.4 ppm, 1 quadruplet and 1 singlet (2 CH₂ groups) and aromatic protons at 7.0 (2H) and 7.3 (d, 1H) ppm. The IR spectrum showed 1 sharp ether band at 1179 cm⁻¹.

Perfume Characteristic:
Initial perfume green, rosemary, citrusal note; after-perfume dusty, animaly, horse's stable note.

Example 6
Fruity Composition for Use in Shampoos:

| | |
|---|---|
| Jasmacyclate | 40 parts |
| Phenirate (H & R) | 5 parts |
| Geraniol | 15 parts |
| Floramat (Cognis) | 20 parts |
| α-Hexyl cinnamaldehyde | 20 parts |
| Rosenoxid L (Dragoco) | 10 parts |
| Herbavert (Cognis) | 30 parts |
| Cyclovertal (Cognis) | 10 parts |
| Methyl dihydrojasmonate | 200 parts |
| Iraldein gamma (H & R) | 30 parts |
| Boisambrene forte (Cognis) | 60 parts |
| Vanillin 10% in DPG | 40 parts |
| Coumarin | 40 parts |
| Iso E super (IFF) | 20 parts |
| Sandelice (Cognis) | 210 parts |
| Astratone | 120 parts |
| 2,4-Dimethyl-2-(2,4-dimethylphenyl)-1,3-dioxolane (Example 2) or DPG | 50 parts |
| Rhuboflor (Firmenich) | 30 parts |
| | 950.0 parts |

The addition of 50 parts of the compound of Example 2 strengthens the fruit character and gives the composition a unique character of black currants. A composition containing DPG (dipropylene glycol) instead of the compound of Example 2 has a comparatively weak fruit character.

Example 7
General Formulation for Fabric Softeners with a Sea Breeze Character

| | |
|---|---|
| Boisambrene forte (cognis) | 210 parts |
| Timberol (Dragoco) | 20 parts |
| Lilial (Givaudan) | 120 parts |
| α-Hexyl cinnamaldehyde | 80 parts |
| Floramat (Cognis) | 20 parts |
| Lyral | 40 parts |
| Sandelice (Cognis) | 10 parts |
| Cyclovertal (Cognis) | 15 parts |
| Anthoxan (Cognis) | 25 parts |
| Dihydroisojasmonate (PFW) | 50 parts |
| Ethyl linalool (Givaudan) | 60 parts |
| Dimetol | 10 parts |
| Troenan (Cognis) | 30 parts |
| Timberol (Dragoco) | 20 parts |
| Citronellol | 40 parts |
| Geranyl nitrile (BASF) | 40 parts |
| Ultralid (PFW) | 30 parts |
| Galaxolid 50% (IFF) | 100 parts |
| 2,5-dimethyl-5-propyl-2-(2,4-dimethylphenyl)-1,3-dioxane (Example 5) or DPG | 40 parts |
| Cyclogalbanat (Dragoco) | 5 parts |
| Ambroxan (Cognis) | 10 parts |
| γ-Decalactone | 5 parts |
| Eugenol | 5 parts |
| Melafleur (IFF) | 10 parts |
| Calone (Pfizer) | 5 parts |
| | 1,000 parts |

The addition of 40 parts of the compound of Example 5 to the mixture enriches the accord with a slightly animaly note strengthening the algal character of the composition. By contrast, a comparison mixture containing 40 parts of APG instead of the compound of Example 5 shows a more flowery character which no longer appears so fresh on laundry.

What is claimed is:

1. A compound of the general formula (I):

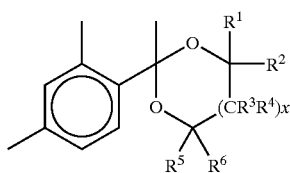

(I)

wherein each of R¹, R², R³, R⁴, R⁵ and R⁶ independently represents a substituent selected from the group consisting of hydrogen, methyl, ethyl, n-propyl, and isopropyl; an wherein x represents either 0 or 1.

2. The compound according to claim 1, wherein each of R¹, R², R³, R⁴, R⁵ and R⁶ independently represents a substituent selected from the group consisting of hydrogen and methyl.

3. The compound according to claim 1, wherein each of R¹, R², R⁵ and R⁶ represents hydrogen and x equals zero.

4. The compound according to claim 1, wherein each of R¹, R² and R⁵ represents hydrogen; R⁶ represents a methyl group and x equals zero.

5. The compound according to claim 1, wherein each of R¹, R², R³, R⁴, R⁵ and R⁶ represents hydrogen and x equals 1.

6. The compound according to claim 1, wherein at least two of R¹, R², R³, R⁴, R⁵ and R⁶ represent a substituent selected from the group consisting of methyl, ethyl, n-propyl, and isopropyl.

7. A perfume composition comprising at least one compound of the general formula (I):

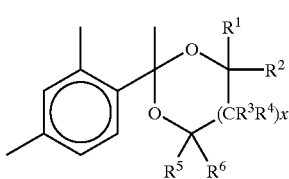

wherein each of $R^1$, $R^2$, $R^3$, $R^4$, $R^5$ and $R^6$ independently represents a substituent selected from the group consisting of hydrogen, methyl, ethyl, n-propyl, and isopropyl; and wherein x represents either 0 or 1; wherein the at least one compound is present in an amount of from 1 to 70% by weight based on the composition.

8. The composition according to claim 7, wherein each of $R^1$, $R^2$, $R^3$, $R^4$, $R^5$ and $R^6$ independently represents a substituent selected from the group consisting of hydrogen and methyl.

9. The composition according to claim 7, wherein each of $R^1$, $R^2$, $R^5$ and $R^6$ represents hydrogen and x equals zero.

10. The composition according to claim 7, wherein each of $R^1$, $R^2$ and $R^5$ represents hydrogen; $R^6$ represents a methyl group and x equals zero.

11. The composition according to claim 7, wherein each of $R^1$, $R^2$, $R^3$, $R^4$, $R^5$ and $R^6$ represents hydrogen and x equals 1.

12. The composition according to claim 7, wherein at least two of $R^1$, $R^2$, $R^3$, $R^4$, $R^5$ and $R^6$ represent a substituent selected from the group consisting of methyl, ethyl, n-propyl, and isopropyl.

13. A method of enhancing the fragrance properties of a composition, said method comprising:

(a) providing a composition to be enhanced;
(b) providing at least one compound of the general formul (I);

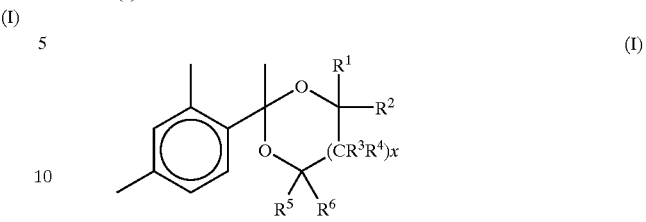

wherein each of $R^1$, $R^2$, $R^3$, $R^4$, $R^5$ and $R^6$ independently represents a substituent selected from the group consisting of hydrogen, methyl, ethyl, n-propyl, and isopropyl; and wherein x represents either 0 or 1; and (c) combining the composition and the at least one compound.

14. The method according to claim 13, wherein each of $R^1$, $R^2$, $R^3$, $R^4$, $R^5$ and $R^6$ independently represents a substituent selected from the group consisting of hydrogen and methyl.

15. The method according to claim 13, wherein each of $R^1$, $R^2$, $R^5$, and $R^6$ represents hydrogen and x equals zero.

16. The method according to claim 13, wherein each of $R^1$, $R^2$ and $R^5$ represents hydrogen; $R^6$ represents a methyl group and x equals zero.

17. The method according to claim 13, wherein each of $R^1$, $R^2$, $R^3$, $R^4$, $R^5$ and $R^6$ represents hydrogen and x equals 1.

18. The method according to claim 13, wherein at least two of $R^1$, $R^2$, $R^3$, $R^4$, $R^5$ and $R^6$ represent a substituent selected from the group consisting of methyl, ethyl, n-propyl, and isopropyl.

* * * * *

UNITED STATES PATENT AND TRADEMARK OFFICE
CERTIFICATE OF CORRECTION

PATENT NO. : 6,864,225 B2
DATED : March 8, 2005
INVENTOR(S) : Markert et al.

It is certified that error appears in the above-identified patent and that said Letters Patent is hereby corrected as shown below:

<u>Title page,</u>
Insert Item:
-- [30]    Foreign Application Priority Data
    May 9, 2000  (DE) ..........................100 22 417 --

Signed and Sealed this

Twenty-fourth Day of May, 2005

JON W. DUDAS
*Director of the United States Patent and Trademark Office*